US007462361B2

(12) United States Patent
Bassiri et al.

(10) Patent No.: US 7,462,361 B2
(45) Date of Patent: Dec. 9, 2008

(54) N,N-DIHALOGENATED AMINO ACIDS AND DERIVATIVES

(75) Inventors: Mansour Bassiri, Davis, CA (US); Ramin Najafi, Novato, CA (US); Lu Wang, Emeryville, CA (US); Jane Yang, Emeryville, CA (US)

(73) Assignee: Novabay Pharmaceuticals, Inc., Emeryville, CA (US)

( * ) Notice: Subject to any disclaimer, the term of this patent is extended or adjusted under 35 U.S.C. 154(b) by 615 days.

(21) Appl. No.: 10/920,636

(22) Filed: Aug. 17, 2004

(65) Prior Publication Data

US 2005/0065115 A1 Mar. 24, 2005

Related U.S. Application Data

(60) Provisional application No. 60/496,207, filed on Aug. 18, 2003.

(51) Int. Cl.
*A61K 9/54* (2006.01)
*C07C 69/86* (2006.01)
(52) U.S. Cl. ......................................... 424/400; 560/66
(58) Field of Classification Search .................. 514/64, 514/561, 553, 601, 612, 114
See application file for complete search history.

(56) References Cited

U.S. PATENT DOCUMENTS 3,966,796 A 6/1976 Kaminski et al. ....... 260/482 R
4,045,578 A 8/1977 Kaminski et al. ........... 424/311
4,386,103 A 5/1983 Pogany et al.
5,096,700 A 3/1992 Seibel et al. .................. 424/52
5,985,239 A 11/1999 Hussain et al. ............. 424/1.11
6,451,761 B1 9/2002 Van Gelder et al.

OTHER PUBLICATIONS

Kaminski, et al., "N-Halo Derivatives IV: Synthesis of Low Chlorine Potential Soft N-Chloramine Systems", Journal of Pharmaceuticals Sciences, vol. 65, No. 12, pp. 1733-1736, (1976).
Kaminski, et al., "N-Halo Derivatives V: Comparitive Antimicrobial Activity of Soft N-Chloramine Systems", Journal of Pharmaceuticals Sciences, vol. 65, No. 12, pp. 1737-1742, (1976).
Kosugi, et al., "N-Halo Derivatives VI: Microbiological and Chemical Evaluations of 3-Shloro-2-oxazolidinones", Journal of Pharmaceuticals Sciences, vol. 65, No. 12, pp. 1743-1746, (1976).
Zawalski, et al., "A Convenient Preparation of N-N-Dibromoamones", Synthetic Communications, 8(8), pp. 549-562, (1978).
Abrantes, S. et al., "Determination of Extractable Biocides in Paper Food Packaging Materials Using Micellar Electrokinetic Chromatography", J. Microcolumn Separations, 10(5) 387-391 (1998).

*Primary Examiner*—James O. Wilson
*Assistant Examiner*—Ebenezer Sackey
(74) *Attorney, Agent, or Firm*—Foley & Lardner LLP

(57) ABSTRACT

The present invention relates to active bactericidal, antibacterial, anti-infective, antimicrobial, sporicidal, disinfectant, antifungal and antiviral compounds and compositions and to new uses of these compositions in therapy. This specification also describes methods of use for the new compounds and compositions. The specification further describes methods for preparing these compounds.

1 Claim, No Drawings

N,N-DIHALOGENATED AMINO ACIDS AND DERIVATIVES

CROSS-REFERENCE TO RELATED APPLICATIONS

This application claims the benefit of U.S. Provisional Application No. 60/496,207 filed Aug. 18, 2003.

FIELD OF THE INVENTION

The present invention relates to bactericidal, antibacterial, anti-infective, antimicrobial, sporicidal, disinfectant, antifungal and antiviral compounds and compositions on the basis of amino acids and their derivatives that have the ability to release halogen and to new uses of these compositions in therapy. In another variation, the present invention relates to active bactericidal, antibacterial, anti-infective, antimicrobial, sporicidal, disinfectant, antifungal and antiviral compounds and compositions and to new uses of these compositions in therapy.

This specification also describes methods of use for the new compounds and compositions. The specification further describes methods for preparing these compounds. More specifically, these halogenated amino acids and their derivatives are also referred to herein as amino acids. Examples of natural amino acids are taurine, homotaurine, alanine, β-alanine, ornithine and γ-glutamic acid, or γ-aminobutyric acid (GABA). Non-exclusive examples of non-natural amino acids starting materials for the preparation of the halogenated amino acids include 1-amino-1-methylethanesulfonic acid, 1-amino-1,1-dimethylethanesulfonic acid, 1,1-dimethyl-2-amino-2-carboxy-ethanesulfonic acid, aminotrimethylene phosphonic acid, 2-amino-5-phosphonopantanoic acid, aminoethylphosponic acid diesters, such as the diethylester, 1-amino-1-methylethane phosphonic acid, 1-amino-2-methylethane phosphonic acid, 1-amino-2-methylpropane phosphonic acid, leucine phosphonic acid, 4-amino-4-phosphonobutyric acid, (±) 2-amino-5-phosphonovaleric acid, (+)2-amino-5-phosphonovaleric acid, d,-1,2-amino-3-phosphonopropionic acid, 2-amino-8-phosphonooctanoic acid, alanine boronic acid, β-alanine boronic acid or leucine boronic acid and their salts.

These starting materials may be used in form of their esters or salts. The lower alkyl esters of the phosphonic acids are the preferred esters for the preparation of the dihalo aminophosphonic acids of the invention and their derivatives. The term halogen as used herein includes chloro, bromo and iodo.

The starting materials for the N,N-dialo amino acids are generally known compounds or may be prepared by known methods. These materials are described in Tetrahedron: Asymmetry 1997, 8 (13), FEMS Microbiol. Lett., 70, 23-28 (1990), Synth. Commun. 2725-2731 (1994), FEMS Microbiol. Lett. 108, 225-230 (1993), Neurosci. Lett. 21: 77-92 (1981), Br. J. Pharmacol. 75, 65, and for example, in Prof. R. Noyori Nobel Lecture 'Asymmetric Catalysis: Science and Opportunities' dated Dec. 8, 2001 (www.nobel.se/chemistry/laureates/2001/noyori-lecture.pdf).

A number of the N,N-dihalogenated amino acids are known. With respect to these amino acids, we provide new compositions with bactericidal, antibacterial, anti-infective, antimicrobial, antifungal and antiviral properties.

The invention also relates to a number of new N,N-dihalogenated amino acids and their derivates with bactericidal, antibacterial, anti-infective, sporicidal, antimicrobial, antifungal, and antiviral properties.

BACKGROUND OF THE INVENTION

A body's immune cells, the neutrophils and macrophages that are known for their abilities to clear infection can generate reactive oxygen metabolites that destroy microorganisms and normal or neoplastic (cancerous) cells and modulate inflammatory responses.

Neutrophils can be activated as a response to inflammatory stimuli, bacterial infection and/or other membrane changes. As a result, they produce super oxide radicals such as: $HOO^{\cdot}$, $O_2^{\cdot}$, and $OH^{\cdot}$. Chloride ion ($Cl^-$) at physiological concentrations of 100-150 mM is oxidized by $H_2O_2$, which is catalyzed by myeloperoxidase (an enzyme within the neutrophils) to form hypochlorous acid (HOCl) and HCl.

Physiological generation of HOCl is tightly regulated through feedback inhibition by an intricate network of biochemical signals. HOCl is generated at a concentration of $2 \times 10^{-7}$ M per $10^6$ activated neutrophils. This quantity of HOCl is estimated to kill approximately $150 \times 10^6$ E. coli bacteria. Once HOCl is produced, it degrades rapidly by reacting with multiple oxidizable substrates within the complex cell system. Thus, the concentrations of reactive oxygen-metabolites are expected to fall to undetectable levels within hours. However, it has been demonstrated that neutrophils can use their HOCl to generate large quantities of a rather long-lived oxidants, such as N-chloramines. These long-lived oxidants are generated as monochloramines of taurine (NCT, or N-chlorotaurine) and dichloramines of taurine (NNDCT, or N,N-dichlorotaurine) depending on the pH of the cellular environment. These oxidants are powerful antimicrobials and play key roles within the defense system as well as modulating the cytokines and growth factors in the host body.

DESCRIPTION OF RELATED ART

German Patent Application 4041703 W. Gottardi describes alkali metal salts of N-chlorotaurine. The application mentions that it has not been possible to isolate N-chlorotaurine as a pure substance but only in the form of a diluted solution when it is prepared in situ. Later work established that N-chlorotaurine could be prepared as described below. The German patent application also describes the preparation of pure alkali metal salts of N-chlorotaurine in crystalline form. It also discloses the use of these salts as disinfectants and bactericides in medicinal applications to humans. The German application describes the preparations of the alkali metal salts by the reaction of taurine with an alkali metal chloramide, such as N-chlorobenzene sulfonamide sodium (Chloramine-B) or N-chloro-4-methyl-benzene sulfonamide sodium (Chloramine-T). Chloramine-B and Chloramine-T are listed in the Merck Index, Thirteenth Edition, 2001, Entries 2084 and 2085 on page 356.

WO0222118 W. Gottardi et al. describe N-chlorotaurine, in particular in the form of its sodium salt as useful for the treatment of fungal infections, such as acute or chronic Rhinosinusitis or other fungal infections such as Otitis, Dermatitis, Bronchititis, diverse forms of pneumonia, such as Pneumocystis carinii, the fungal infections of sex organs, such as Colpitis, Endometritis, Balnitis, fungal infections of the gastrointestinal tract, such as Stomatitis, Oesophagitis, Enteritis, or fungal infections of the urethra, such as Pyelonephrititis, Ureteritis, Cystitis, or Urethritis.

Recently Gelder et al. have synthesized and isolated N,N-dichlorotaurine as a powder (Gelder, N. M.; Bowers, R. Synthesis and characterization of N,N-dichlorinated amino acids: Taurine, Homotaurine, GABA and L-Leucine J. Neurochemical Research. 2001; 26:575-578). N-chlorotaurine (NCT) and N,N-dichlorotaurine (NNDCT) can be identified by their UV spectra. NNDCT has a maximum absorbance at 302 mM with a molar absorptivity of 332.9 M$^{-1}$ cm$^{-1}$. These values are from Gottardi, W.; Nagl, M. *Arch. Pharm. Med. Chem.* 2002, 9, 411-421. NCT has a maximum absorbance at 252 nm with a molar absorptivity of 415 M$^{-1}$ cm$^{-1}$.

Juan M. Antelo et al., *J. Chem. Soc., Perkin Trans.* 2, 2000, 2109-2114 described the general acid-base catalysis in the reversible disproportionation reaction of N-chlorotaurine. The authors also describe the preparation of solutions of N,N-dichlorotaurine by disproportionation of N-chlorotaurine at pH 2-2.5 and the stability of N,N-dichlorotaurine at pH=1.88. The loss of N,N-dichlorotaurine was less than 5% after 100 hours.

SUMMARY OF THE INVENTION

It is understood that any aspect or feature of the present invention whether characterized as preferred or not characterized as preferred may be combined with any other aspect or feature of the invention, whether such other feature is characterized as preferred or not characterized as preferred. For example, a feature described as preferred, for example a pH range, or a specific pH for a particular composition (for example, certain N,N-dihalo amino acids of a specific formula) may be combined with another composition (N,N-dihalo amino acids of another specific formula) without deviating from the present invention. This statement also applies to any combination of substituents. For example, a substituent characterized as preferred may be combined with any other substituent not characterized as preferred. Accordingly, in its broadest aspects the present invention provides pharmaceutical compositions which include an N,N-dihaloamino acid of the formula (I)

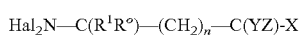

or a derivative thereof. A is hydrogen or Hal$_2$N— wherein Hal is halogen selected from the group consisting of chloro, bromo and iodo; R is a carbon carbon single bond or a divalent cycloalkylene radical with three to six carbon atoms, R$^1$ is hydrogen, lower alkyl or the group —COOH; R$^°$ is hydrogen or lower alkyl; n is 0 or an integer from 1 to 13, or R$^1$ and R$^°$ together with the carbon atom to which they attach form a (C$_3$-C$_6$)cycloalkyl ring; Y is hydrogen, lower alkyl or —NH$_2$ or —NHal$_2$; and Z is hydrogen or lower alkyl; and X' is hydrogen, —COOH, —CONH$_2$, —SO$_3$H, —SO$_2$NH$_2$, —P(=O)(OH)$_2$ or —B(OH)$_2$. If R is a divalent cycloalkylene radical n will not exceed the integer 11. That is, n may be 0, 1, 2, 3, 4, 5, 6, 7, 8, 9, 10, or 11. In other words the amino acid including the acidic group X will have up to 16 chain atoms. In the divalent cycloalkylene radical or in the divalent radical —CH$_2$)$_n$— one hydrogen may be substituted with —NHal$_2$. While the N,N-dihaloamino acids of the invention may contain up to 3 —NHal$_2$ groups, N,N-dihaloamino acids with 1 or 2 —NHal$_2$ groups are preferred. Most preferred are N,N-dihaloamino acids with 1 —NHal$_2$ group. This group may be in alpha-, beta-, gamma-, delta-, epsilon-, etc. to omega-position of the acidic groups R$^1$ (if R$^1$ is —COOH) or X'.

Derivatives of the compounds of formula I include pharmaceutically acceptable salts, esters with lower alkanols, lower alkanoyl derivatives of the —NH$_2$ group attached to the carbon atom to which the substituent X' is attached. The term "lower" in this respect includes residues with 1 to 6, preferably 1 to 4 carbon atoms.

In a preferred embodiment R is a carbon carbon single bond and n is 0 or an integer from 1 to 7, more preferably 0 or an integer from 1 to 5, and most preferably 0 or an integer from 1 to 3, that is 1, 2 or 3. Also of interest are the N,N-dihalo amino acids in which n=4 or n=5 or n=6 or n=7 or n=8 or n=9.

A preferred composition of the invention comprises a composition having a concentration of the N,N-dihaloamino acid or its derivative between 0.1 to 100 mM and a pH range between about 3 to about 4.8, 3.0 to 4.5, or 3.5 to 4.5, or at about 3.5.

Another composition has a concentration of the N,N-dihaloamino acid or its derivative between 0.1 to 50 mM and a pH range between about 2 to about 7, about 3 to about 6, 3 to about 4.8, about 3 to 4.5, or 3.5 to 4.5, or at about 3.5.

The present invention also provides new bactericidal, antibacterial, anti-infective, antimicrobial, sporicidal, disinfectant, antiviral and antifungal compositions which include an N,N-dihalo-amino acid of the formula (II)

or a derivative thereof.

In the formula Hal is halogen selected from the group consisting of chloro, bromo and iodo; R$^1$ is hydrogen, lower alkyl or the group —COOH; R$^°$ is hydrogen or lower alkyl, or R$^1$ and R$^°$ together with the carbon atom to which they attach form a (C$_3$-C$_6$)cycloalkyl ring; n is 0 or an integer from 1 to 3; Y is hydrogen, lower alkyl, —NH$_2$ or —NHal$_2$; and Z is hydrogen or lower alkyl; and X is —COOH, —CONH$_2$, —SO$_3$H or —SO$_2$NH$_2$.

Derivatives of the compounds of formula II include pharmaceutically acceptable salts, esters with lower alkanols, lower alkanoyl derivatives of the —NH$_2$ group attached to the carbon atom to which the substituent X is attached. The term "lower" in this respect includes residues with 1 to 6, preferably 1 to 4 carbon atoms.

The pharmaceutically acceptable salts of compounds of formula (I), (II), (III) or (IV) include salts with pharmaceutically acceptable cations. The compounds of formula (III) and (IV) are described below. The salts of the N,N-dihaloamino acid includes salts of bases with the —COOH, —CONH$_2$, —SO$_3$H or —SO$_2$NH$_2$ groups. Pharmaceutically acceptable salts also include ammonium, alkali metal, magnesium, or calcium salts and any organic amine salts. Alkali metal salts, Mg, Ca and Al salts are of interest. The alkali metal salts are of particular interest, particularly lithium, sodium, or potassium salts.

Examples of acid addition salts include, but are not limited to, mineral or organic acid salts of basic residues such as amines; alkali or organic salts of acidic residues such as carboxylic acids, and the like. Pharmaceutically acceptable salts include, but are not limited to, hydrohalides, sulfates, methosulfates, methanesulfates, toluenesulfonates, nitrates, phosphates, maleates, acetates, lactates and the like.

Lists of suitable salts are found in Remington's Pharmaceutical Sciences, 17th ed., Mack Publishing Company, Easton, Pa., 1985, p. 1418 or The Merck Index, Thirteenth Edition, 2001, Published by Merck Research Laboratories Division of Merck & Co., Inc. on pages MISC-22 and MISC-23, the disclosures of which are hereby incorporated by reference in their entirety.

The pharmaceutically acceptable acid addition salts of the —NH$_2$ group attached to the carbon atom to which substituent X is attached include salts among others with hydrochloric, sulfonic, phosphoric, nitric acid, benzenesulfonic, toluenesulfonic, methanesulfonic acid, camphorsulfonic acid and other acids.

Further derivatives of the compounds of formulae (I), (II), (III), and (IV) include esters of the groups —COOH or —SO₃H with lower alkanols and lower alkanoyl derivatives of the amino group attached to the carbon atom to which substituent X is attached.

Further derivatives of the compounds of formulae (I), (II), (III), and (IV) also include N,N-dihalo-amino acids in which certain groups of the amino acid molecule are protected by protecting groups. "Protecting group" means a chemical group that (a) preserves a reactive group from participating in an undesirable chemical reaction; and (b) can be easily removed after protection of the reactive group is no longer required.

"Amino-protecting group" means a protecting group that preserves a reactive amino group that otherwise would be modified by certain chemical reactions. Non-limiting examples of amino protecting groups include the formyl group or lower alkanoyl groups with 2 to 4 carbon atoms, in particular the acetyl or propionyl group, the trityl or substituted trityl groups, such as the monomethoxytrityl group, dimethoxytrityl groups such as the 4,4'-dimethoxytrityl or 4,4'-dimethoxytriphenylmethyl group, the trifluoroacetyl, and the N-(9-fluorenyl-methoxycarbonyl) or "FMOC" group, the allyloxycarbonyl group or other protecting groups derived from halocarbonates such as ($C_6$-$C_{12}$)aryl lower alkyl carbonates (such as the N-benzyloxycarbonyl group derived from benzylchlorocarbonate), such as the benzyloxycarbonyl (CBZ group), or derived from biphenylalkyl halo carbonates, or tertiary alkyl halo carbonates, such as tertiary-butylhalocarbonates, in particular tertiary butylchlorocarbonate, or di(lower)alkyldicarbonates, in particular di(t-butyl)-dicarbonate, and the phthalyl group.

The term "composition" as used herein, refers to various forms of the compounds or compositions of the present invention, including solids such as powders, mixtures of powders and the like, emulsions, suspensions as well as solutions.

In one aspect, the compositions and their uses include known N,N-dihaloamino acids or their derivatives. In another aspect the compositions and their uses include new N,N-dihaloamino acids or their derivatives. In either instance the compositions may be maintained in acidic form, that is at a pH below 7, for example 6.8, that is at a pH between about 2 to about 7, that is at a pH range between 2.0 to 6.8, 2.5 to 6.5, 2.5 to 6.0, or 2.5 to 5.0, or 3.0 to 5.0, or at a pH of about 3.5. Under different circumstances the pH may be kept below 5, that is, at a pH range of about 3 to 4.5, or 3.5 to 4.5, or at a pH about 3.5. The key is that the pH of the composition is acidic. The selection of the pH will depend on many factors, including the specific use of the N,N-dihaloamino acid (whether in vitro or in vivo), the type of the infection treated (for example, whether the infection is caused by bacteria, yeast, fungi or viruses), the site of the infection (for example, whether it is an infection of the eye, the larynx or the urethra or any target tissue or organ), the severity of the infection, the sensitivity of the patient, etc.

In another aspect the composition, the solutions of the invention contain N,N-dihaloamino acids in the concentration range of 0.1 to 100 millimolar (mM).

In a further aspect the composition will be isotonic and physiologically balanced.

The N,N-dihaloamino acids differ significantly from HOCl because they maintain an oxidizing potential with significant bactericidal activities, and yet they are less toxic than HOCl. N,N-dihaloamino acids are also stable enough to diffuse some distance before oxidizing susceptible target molecules. The low molecular weight N,N-dihaloamino acids of the present invention with n=0 or an integer up to 5 are more hydrophilic molecules.

Surprisingly, it has been found that, while the N,N-dihaloamino acids of the invention have strong bactericidal, antibacterial, anti-infective, antimicrobial, sporicidal, disinfectant, antifungal and antiviral, they have low cytotoxicity.

In a further aspect the compositions of the invention are stabilized to meet the requirement of being useable as compositions for the treatment or prevention of bacterial, microbial, spore, fungal and viral infections or contaminations.

In another aspect the stabilization of the composition is provided by storing the compositions in a receptacle that will ensure sufficient stability to control bacterial, microbial, spore, fungal and viral infections or contaminations.

The present invention provides pharmaceutical compositions which include an N,N-dihaloamino acid of the formula (III)

or a derivative thereof. A is hydrogen or Hal₂N— wherein Hal is halogen selected from the group consisting of chloro, bromo and iodo; R is a carbon carbon single bond or a divalent ($C_3$-$C_6$)cycloalkylene radical with three to six carbon atoms, $R^1$ is hydrogen, lower alkyl or the group —COOH; $R^2$ is lower alkyl or $R^1$ and $R^2$ together with the carbon atom to which they attach form a ($C_3$-$C_6$)cycloalkyl ring; n is 0 or an integer from 1 to 13; Y is hydrogen, lower alkyl or —NH₂ or —NHal₂; and Z is hydrogen or lower alkyl; and X' is hydrogen, —COOH, —CONH₂, —SO₃H, —SO₂NH₂, —P(=O)(OH)₂ or —B(OH)₂. If R is a divalent ($C_3$-$C_6$)cycloalkylene radical n will not exceed the integer 11. In other words the amino acid including the acidic group X' will have up to 16 chain atoms. Optionally, in the divalent ($C_3$-$C_6$)cycloalkylene radical or the divalent radical —(CH₂)ₙ—, one hydrogen may be substituted with —NHal₂. While the N,N-dihaloamino acids of the invention may contain up to 3 —NHal₂ groups, N,N-dihaloamino acids with 1 or 2 —NHal₂ groups are preferred. Most preferred are N,N-dihaloamino acids with 1 —NHal₂ group. This group may be in alpha-, beta-, gamma-, delta-, epsilon-, etc. to omega- position of the acidic groups $R^1$ (if $R^1$ is —COOH) or X'.

Derivatives of the compounds of formula III or IV (described below) include pharmaceutically acceptable salts, esters with lower alkanols, lower alkanoyl derivatives of the —NH₂ group attached to the carbon atom to which the substituent X or X' is attached. The term "lower" in this respect includes residues with 1 to 6, preferably 1 to 4 carbon atoms.

In a preferred embodiment R is a carbon carbon single bond and n is 0 or an integer from 1 to 7, more preferably 0 or an integer from 1 to 5, and most preferably 0 or an integer from 1 to 3.

In another aspect a composition with bactericidal, antibacterial, anti-infective, antimicrobial, sporicidal, disinfectant, antifungal and antiviral activity is provided comprising an N,N-dihaloamino acid of the formula (IV)

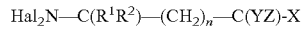

or a derivative thereof; wherein Hal is halogen selected from the group consisting of chloro, bromo and iodo; $R^1$ is hydrogen, lower alkyl or the group —COOH; $R^2$ is lower alkyl or $R^1$ and $R^2$ together with the carbon atom to which they attach form a ($C_3$-$C_6$)cycloalkyl ring; n is 0 or an integer from 1 to 3; Y is hydrogen, lower alkyl or —NH₂; and Z is hydrogen or lower alkyl; and X is —COOH, —CONH₂, —SO₃H or —SO₂NH₂; said derivative being selected from the group consisting of pharmaceutically acceptable salts, esters with lower alkanols, and lower alkanoyl derivatives of the —$NH_2$ group attached to the carbon atom to which the substituent X is attached.

In another aspect, the above-described composition comprising a new N,N-dihaloamino acid of the formula (IV) is one in which $R^1$ is hydrogen, or lower alkyl; n is 0, 1 or 2; Y is hydrogen or lower alkyl; Z is hydrogen or lower alkyl; and X is —$SO_3H$ or —$SO_2NH_2$; or a derivative thereof; said derivative being selected from the group consisting of pharmaceutically acceptable salts or esters with lower alkanols.

In a further aspect, the above-described compositions comprising a new N,N-dihaloamino acid of the formula (IV) are ones in which wherein Y and Z are hydrogen; X is —$SO_3H$; said derivative being selected from the group consisting of pharmaceutically acceptable salts.

In another aspect, Hal is chloro.

The preferred derivatives are pharmaceutically acceptable salts.

In another aspect, the above-described compositions include the following compounds or a derivative thereof; said derivative being selected from the group consisting of pharmaceutically acceptable salts and esters with lower alkanols:
N,N-dichloro-2,2-dimethyltaurine;
N,N-dichloro-1,1,2,2-tetramethyltaurine;
N,N-dibromo-2,2-dimethyltaurine;
N,N-dibromo-1,1,2,2-tetramethyltaurine;
N,N-diiodotaurine;
N,N-dichloro-2-methyltaurine;
N,N-dichloro-2,2,3,3-tetramethyl-β-alanine;
N,N-dichloro-3,3-dimethylhomotaurine;
N,N-dichloro2-methyl-2-amino-ethanesulfonic acid; and
N,N-dichloro-1-methyl-ethanesulfonic acid,
N,N-dichloro aminotrimethylene phosphonic acid;
N,N-dibromo 2-amino-5-phosphonopantanoic acid;
N,N-dichloro aminoethylphosponic acid diesters, such as the diethylester;
N,N-dichloro 1-amino-1-methylethane phosphonic acid;
N,N-dichloro 1-amino-2-methylethane phosphonic acid;
N,N-dichloro 1-amino-2-methylpropane phosphonic acid;
N,N-dichloro leucine phosphonic acid;
N,N-dichloro 4-amino-4-phosphonobutyric acid;
(±) N,N-dichloro 2-amino-5-phosphonovaleric acid;
N,N-dichloro (+)2-amino-5-phosphonovaleric acid;
N,N-dichloro d,1-2-amino-3-phosphonopropionic acid;
N,N-dichloro 2-amino-8-phosphonooctanoic acid;
N,N-dichloro leucine boronic acid or
N,N-dichloro-β-alanine boronic acid or a pharmaceutically acceptable salt or ester thereof.

In another aspect, the compositions described herein comprising an N,N-dihaloamino acid of the formula (I), (II), (III) or (IV) or their derivatives are ones in which Hal is chloro.

In another aspect, the compositions of the invention further comprises a pharmaceutically acceptable carrier.

The phosphonic or boronic acids of the invention may be combined with a dihydroxy compound with up to ten carbon atoms which may be acyclic or cyclic having at least two hydroxyl groups attached to two different carbon atoms, such as ethylene glycol, 2-amino-2-(hydroxymethyl)-1,3-propane diol, mannitol, diethylene glycol, 1,2-hexane diol, glycerol, diethanolamine, pinacol or other similar dihydroxy compounds. In some cases this combination enhances the stability of the boronic or phosphonic acids of the invention.

Again, all the features, characteristics and ranges described for the invention, in any aspect, whether described as of interest or as particular or not, may be combined with each other. For example, a substituent of interest in the formulae depicted herein may be combined with another more broadly defined, not emphasized substituent described herein. For example, the substituent X being —$SO_3H$ may be combined with substituents Y or Z other than hydrogen.

Processes for the Preparation of N,N-Dihalo-amino Acids and Derivatives

The N,N-dihaloamino acids and derivatives are prepared by the reaction of the amino acid or a derivative thereof from which the halogenated amino acids are produced with a halogen source under reaction conditions which lead to the replacement of two hydrogen atoms at the -amino group of the amino acid with two halogen atoms, that is chloro, bromo or iodo atoms. These processes are known to chemists skilled in the art.

In one aspect of the invention, the amino acids that are used as starting materials include taurine, homotaurine, β-alanine, ornithine and γ-glutamic acid, and γ-aminobutyric acid (GABA), 1-amino-1-methylethanesulfonic acid, 1-amino-1, 1-dimethylethanesulfonic acid or 1,1-dimethyl-2-amino-2-carboxy-ethanesulfonic acid, and others. For example, aminotrimethylene phosphonic acid or its salts, 2-amino-5-phosphonopantanoic acid or its salts, aminated (1R,2S)-(1,2-epoxypropyl)phosphonic acid (or aminated fosfomycin), aminoethylphosponic acid diesters, such as the diethylester, 1-amino-1-methylethane phosphonic acid, 1-amino-2-methylethane phosphonic acid, 1-amino-2-methylpropane phosphonic acid, leucine phosphonic acid, 4-amino-4-phosphonobutyric acid, (±)2-amino-5-phosphonovaleric acid, (+)2-amino-5-phosphonovaleric acid, d,1-2-amino-3-phosphonopropionic acid or 2-amino-8-phosphonooctanoic acid may be used. In another aspect, these starting materials may be used in form of their esters or salts. In another aspect, the lower alkyl esters of the phosphonic acids are the preferred esters for the preparation of the dihalo phosphonic acids of the invention and their derivatives. All these starting materials are either well-known, commercially available, or may be prepared by well-known methods of preparation. A number of the starting materials are commercially available, for example from Sigma-Aldrich.

The following non-exclusive halogen sources may be used to produce the N,N-dihaloamino acids and their derivatives: HOCl or its salts (for example, NaOCl or KOCl), N-haloarylsulfonamide salts, wherein the aryl group contains from 6 to 15 carbon atoms with 1 or 2 aromatic rings, 6 to 10, or 6 to 8, carbon atoms and one aromatic ring, such as N-halobenzenesulfonamide or N-halo-4-alkylbenzenesulfonamide, wherein the alkyl group is lower alkyl from 1 to 4 carbons, methyl or ethyl. The N-halobenzene-sulfonamides or N-halo-4-alkyl-benzenesulfonamides are often used in form of their salts, for example, alkali salts, for example, their sodium or potassium salts. The most frequently used reagents will be N-chlorobenzenesulfonamide and N-chloro-4-methyl-benzenesulfonamide in form of their sodium salts, because they are readily commercially available. Other non-limiting halogen releasing agents or sources may be $HClO_2$, N-chloro-succinimide or N-bromosuccinimide, N-iodosuccinamide, $Cl_2$, $Br_2$, $I_2$, thionylchloride, phosgene, $PCl_3$, $PCl_5$, and chlorinating agents, such as those used in swimming pools, or combinations of the agents.

Other amino acid starting materials include 2,2-dimethyl-hypotaurine, 1,1,2,2-tetramethyl-hypotaurine, 2,2-dimethyl-taurine, 1,1,2,2-tetramethyltaurine, 2,2,3,3-tetramethyl-β-alanine, and 3,3-dimethylhomotaurine.

If one molecule of the halogen source releases one halogen, obviously for each starting amine of the amino acid or derivative molecule at least two molecules of the halogen source will be used. More details of the preparation of N,N-dihaloamino acids and their derivatives are set forth in the examples.

When not commercially available the phosphonic acid starting materials for the preparation of the compounds of the present invention may be prepared according to procedures well known to one skilled in the art. See for example Yuan, C. et al, New Strategy for the Synthesis of Functionalized Phosphonic Acids, Heteroatom Chem. 1997, 8 (2) 102-122; Yuan, C., et al., New strategy for the Synthesis of Functionalized Phosphonic Acids, Pure Appl. Chem. 1996, 68(4), 907-12; A Versatile Route to Substituted Organophosphonic Acids, J. Am. Chem. Soc., 1990, 31, 2933; G. M. Kosolapoff, The Synthesis of Phosphonic and Phosphinic Acids, Organic Reactions, Vol. 6 (1951), and references cited therein.

The boronic acid starting materials and their esters are available commercially from, for example, Acros Organics (Fischer Scientific) or Ryscor Science, Inc. (Raleigh, N.C.), among other companies, or may be prepared according to procedures known to one skilled in the art. See for example, Webb, K. S. and Levy D. Tetrahedron Lett. 1995, 36, 5117; Suzuki, A. Pure Appl. Chem. 1994, 66, 213; Miyaura, N. and Suzuki, A. Chem. Rev. 1995, 95, 2457-2483; Suzuki, A. J. Organometallic Chem. 1999, 576, 147-168; Kamatani, A. and Overman, L. E. J. Org. Chem. 1999, 64, 8743-8744, Yang, W.; Gao, S.; Wang, B. "Boronic Acid Compounds as Potential Pharmaceutical Agents" Med. Res. Rev. 2003, 23, 346-368, and references cited therein and Brown, H. C.; Midland, M. M.; Levy, A. B.; Kramer, G. W., "Organic Synthesis via Boranes" Wiley-Interscience: New York, 1975.

Compounds according to the present invention can also include their individual stereoisomers (enantiomers and diastereoisomers) as well as the racemic mixtures of the compound. The individual isomers, such as the pure R, S, RR, SS, RS, SR, etc. may be prepared by treating the isomeric mixture with an optically active resolving agent to form a pair of diastereoisomeric compounds. The diastereoisomeric compounds may be separated and the optically pure enantiomer or diastereomer may be isolated using procedures well known in the art. Because diastereomers have distinct physical properties (such as the melting points, boiling points, solubilities, reactivity, etc.), they can be readily separated by taking advantage of these dissimilarities. The diastereomers can be separated by chromatography or, preferably, by separation or resolution techniques based upon differences in solubility. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981) and references cited therein.

A typical reaction scheme to prepare the N,N-dihaloamino acids can be depicted as follows:

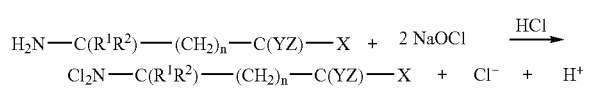

in which $R^1$, $R^2$, n, X, Y and Z have the above-described meanings.

The amino acid starting material is dissolved in a lower alkanol (for example, methanol or ethanol) and made acidic. To this solution an aqueous NaOCl solution is added. The reaction results in the chlorination of the amino group and the precipitation of sodium chloride. The solvent is evaporated at low temperatures, for example, below 30° C. and a residue is obtained. The residue is taken up in a solvent and the N,N-dihaloamino acid isolated by extraction with a solvent not miscible with the aqueous lower alkanol phase. Similarly the N,N-dihalo-amino acid may be prepared by reacting the amino acid starting material with HOCl.

Accordingly, the bromo analogs may also be prepared with NaOBr as the halogenating agent.

According to J Marcinkiewicz et al. 2000 (J of Inflammatory Research 49, 280-289) NNDCT (N,N-dichlorotaurine) may be synthesized in solution by reacting HOCl with taurine at pH 5. NNDCT also can be generated in the oxidation of Bunte salt ($H_2NCH_2CH_2S$—$SO_3H$) (Chinake et al. Oxyhalogen-sulfur chemistry: kinetics and mechanism of the oxidation of a Bunte salt 2-aminoethanethiolsulfuric acid by chlorite. Phys. Chem. Chem. Phys. 2001; 3:4957-4964) and hypotaurine ($H_2NCH_2CH_2SO_2H$) by chlorite ($ClO_2^-$) (Martincigh, B. S.; Mundoma, C.; Simoyi, R. H.; Antioxidant chemistry: Hypotaurine-taurine oxidation by chlorite. J. Phys. Chem. A. 1998; 102:9838-9846).

The reactions are shown in equations 1-6:

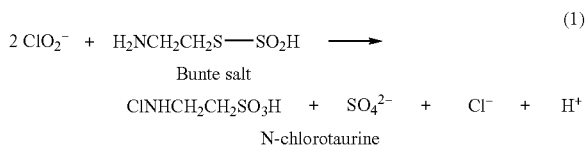

N-chlorotaurine disproportionates to form N,N-dichlorotaurine and taurine in acidic solution:

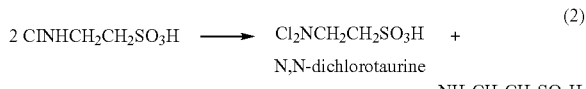

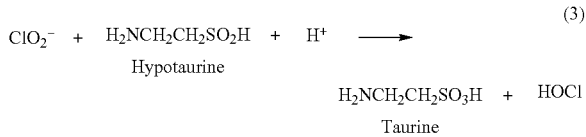

HOCl can rapidly oxidize the remaining hypotaurine to taurine:

or oxidize hypotaurine to N-chlorohypotaurine:

In highly acidic conditions, HOCl oxidizes N-chlorohypotaurine to N,N-dichlorotaurine.

The compounds with at least one lower alkyl group attached to the carbon atom to which the amino group is attached are more stable dihalogenated amino acids.

These compounds may be prepared as follows:

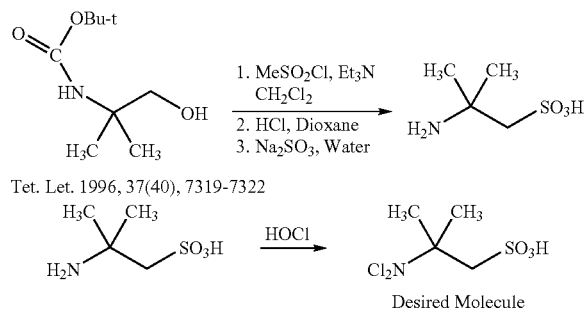

Tet. Let. 1996, 37(40), 7319-7322

Derivatives of the N,N-dihalo-amino acids may be prepared by protecting the amino group with an amino-group protecting agent as disclosed herein, for example, by forming the benzyloxycarbonyl (CBZ) derivative, followed by the formation of the sulfonyl chloride which may be converted into sulfonamides, for example with a lower alkyl amine, such as methylamine. Similarly, the sulfonyl chloride may be reacted with benzylamine, and tile resulting benzylsulfonamide may be converted to the group —$SO_2NH_2$. Thereafter the protecting group may be removed by methods known per se to chemists skilled in the art. A comprehensive list of suitable protecting groups that may be used may be found in T. W. Greene, *Protecting Groups in Organic Synthesis*, 3rd edition, John Wiley & Sons, Inc. 1999.

Pharmaceutically-acceptable salts of the compounds of the invention may be prepared by reacting the free acid or base forms of these compounds with a stoichiometric or greater amount of the appropriate base or acid in water or in an organic solvent, or in a mixture of the two; generally, for example, non-aqueous media like ether, ethyl acetate, ethanol, isopropanol. The salts of the invention may also be prepared by ion exchange, for example.

Salts may also be prepared by reacting the N,N-dihaloamino acids in other manners known per se including a method analogous to the method described in German Patent Application 4041703 W. Gottardi.

The sodium salts of the N,N-dihaloamino acids may be converted into the lower alkyl esters by reacting the sodium salt with a lower dialkyl sulfate, such as dimethyl or diethyl sulfate in the presence of sodium bicarbonate.

The amides in which the substituent X or X' is —$CO$—$NH_2$ are produced in a manner well-known to chemists skilled in the art.

Methods of Use for the N,N-Dihaloamino Acids and Derivatives

The N,N-dihaloamino acids and their derivatives are antimicrobial agents which kill microbes at relatively low concentrations and can be tolerated by eukaryotic cells at significantly high concentrations. This range of therapeutic activity and favorable therapeutic index is absolutely critical considering the physiological role of chloramines in the destruction of pathogens in vivo. For an antimicrobial product that is applied to tissues such as ophthalmic, skin or any other sensitive areas its safety and efficacy cannot be compromised. Thus, use of such product(s) in humans for treating infections is supported by our positive results.

The compounds of Formulae (I), (II), (III), or (IV) have the following potential areas of application: contact lens cleanser, bacterial inactivation, ophthalmic, general surgical preparation, surgical instrument disinfection, medical device and instrument disinfection, dental instruments disinfection and application in food sanitation including disinfection of surface areas. They are also useful in vaccine formulations (as preservative and potentially adjuvant), as compounds with viricidal effect, for the viral inactivation of both DNA and RNA classes of viruses including HIV, hepatitis A, respiratory syncytial virus, West Nile virus, HSV-1, HSV-2, SARS, influenza and para-influenza viruses, picornaviruses, and vaccinia virus (as a Model for Poxviruses). In addition, these compounds are also useful for the treatment of fungal infections, such as acute or chronic Rhinosinusitis or other fungal infections such as Otitis, Dermatitis, Bronchititis, Pneumonia's such as Pneumocystis carinii, the fungal infections of sex organs, such as Colpitis, Endometritis, Balnitis, fungal infections of the gastrointestinal tract, such as Stomatitis, Oesophagitis, Enteritis, or fungal infections of the urethra, such as Pyelonephrititis, Ureteritis, Cystitis, or Urethritis. Furthermore, the compositions described herein have antimicrobial activity against many other microorganisms, including *Escherichia coli*, *Listeria monocytogenes*, *Staphylococcus aureus*, methicillin-resistant *S. aureus* (MRSA), *Pseudomonas aeruginosa*, *Lactobacillus*, yeast, vancomycin-resistant enterococcus, molds, and spores, including spores of anthrax. In particular, the solutions of the present invention may be useful in the treatment of several different strains of *Bacillus anthracis*. Vancomycin-resistant bacteria, MRSA, and others are easily destroyed by the compositions of the present invention.

In a further aspect of the invention, there is provided a method for the treatment of various medical conditions selected from the groups consisting of promoting wound healing, reduction of pathogens in open wounds, wound decontamination, ocular disinfection or decontamination, oral disinfection, antifungal therapy, ophthalmic, oral surgery and dentistry, otology applications, reduction of pathogens in pulmonary infections, reduction of pathogens in burns, lavage, reduction of infectious load in organs for transplantation, reduction of bacterial load in autologous or artificial tissue transplantation, oral disinfection antifungal therapy, treatment of biofilm for cystic fibrosis or other diseases that produces biofilms, treatment of viral infections, treatment of skin diseases, and tissue repair and regeneration, which method comprises using the solution of the invention by applying the solution to the site where treatment is required.

The dosage for use on chronic wounds of an approximate size of 25 square cm might be in the range of 30 ml of solution containing 2 to 200 mg of active ingredient where the active ingredient is NNDCT applied one to ten times per day. In certain instances the composition may contain 0.1 to 100 mM of active ingredient. Dosages in other applications would be adjusted to the surface area depending on where the antimicrobial activity is required and the severity of infection.

The Compositions of the Invention

In one aspect the compositions in form of solutions are osmotically balanced, and have minimal cytotoxicity.

In another aspect the compositions described herein have a therapeutic index of about 1000 to about 5,000, defined by the ratio of their 50% inhibitory concentration cytotoxicity index ($IC_{50}$) at one hour against both L929 mouse lung epithelial cells and primary human fibroblasts to their Minimum Bactericidal Concentration against *Escherichia coli* ATCC 11229 at 37° C. for one hour.

Because the compositions of the present invention are non-toxic and have antibacterial properties, they are useful in any application in which antimicrobial properties are desirable.

Such applications include, without limitation, treatment of wounds, burns, and canker sores; irrigation; cleaning of tissue sites (e.g., pre- and post-operative); ophthalmic applications (e.g., in contact lens cleaning solutions or for irrigation of the eye before, during, or post ophthalmic surgery); for dermatological applications, psoriasis; and numerous applications which are readily apparent to one skilled in the art. Application also includes the elimination or reduction of pathogens on surfaces including medical equipment, instruments, devices or food (without limiting to meat, fruits, vegetables) and food contact surfaces including the elimination or reduction bacterial biofilms. Unlike many anti-infective compositions used in similar applications, the compositions of the invention have minimal to no side effects.

The compositions of the invention which comprise N,N-dihaloamino acids of the formulae (I), (II), (III) or (IV) and their derivatives may be incorporated into a variety of applications, including bandages or wound dressings. The compositions in form of physiologically balanced, acidic solutions may be used in combination with specially designed bandages in a wound treatment protocol. The specialized bandage may include an opening or "window" through which topical treatment materials such as the solution of the present invention may be applied.

Also disclosed herein is an article of manufacture comprising the composition of the invention packaged in a container. Surfaces of the container which are in contact with the composition of the invention are made of material which is not reactive with an oxidizing agent.

The stability of a solution of N,N-dihaloamino acids and their derivatives permits the use of different forms of packaging that would be practical for use by patients. The solution may be packaged in several single-use 30 ml amber glass bottles with Teflon-lined screw caps and sealed with tape to ensure gas tightness. In one aspect, the same solution may be packaged in a 250 ml amber glass bottle or in a 250 ml non-reactive plastic bottle. However, up to 5 liter bottles may be used, because such larger volumes are practical for treatment of burns. Storage in these receptacles ensures long-term stability required for the uses of the compositions described herein in detail. For example, a solution of N,N-dichlorotaurine within the concentration range described herein in a vial stored in a refrigerator will have a loss of no more than 13% of N,N-dichlorotaurine at time t=0 after a period of three months. Additionally, packaging may include a dual chamber system where component A is mixed with component B to form the final product, NN-dihaloamino acid or its derivatives.

In one aspect, the solutions of the present invention may be stored in single-use containers. In another aspect, the solutions of the invention may be stored in single-use containers of various different sizes, configurations, and having different volumes as suitable for the desired applications as disclosed herein. In some applications, for example, the solution of the invention may be stored in single-use 30 mL, optionally disposable containers. In one aspect the present composition may be stored as powder together with pharmaceutically accepted excipients under inert gas at room temperature.

The compositions of the invention may include the following pharmaceutically acceptable carriers: sodium chloride to attain isotonicity, buffers, stabilizers, solvents, flavoring agents (in case of oral or nasopharyngeal administration and food industry), preserving agents, diluents, extenders and other auxiliary substances or excipients. Specific examples of pharmaceutically acceptable carriers and excipients that may be used are described in Remington: The Science and Practice of Pharmacy, A. Gennaro, ed., 20th edition, Lippincott, Williams & Wilkins, Philadelphia, Pa.; Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995), the disclosures of which are incorporated herein in their entirety. In general, water, a suitable oil, saline, lower alcohols, and glycols such as propylene glycol or polyethylene glycols may be suitable carriers for solutions. In one aspect solutions contain the active ingredient in a water soluble or aqueous medium soluble form, for example as a salt, together with suitable stabilizing agents, and if necessary, buffer substances. In addition, solutions may contain preservatives, such as benzalkonium chloride, methyl- or propyl-paraben, and chlorobutanol. Suitable pharmaceutical carriers are described in Remington: The Science and Practice of Pharmacy, the above-identified standard reference text in this field.

The compositions may further comprise other active ingredients, such as HOCl or other antibacterials as long as they do not interfere with the stability or function of the N,N-dihaloamino acids of the invention.

The amounts or concentrations of N,N-dihaloamino acid in the compositions of the invention may vary over broad ranges. For example, a composition may contain from 0.001 to 100% by weight of the composition of the N,N-dihaloamino acid. In case of 100%, the composition may be applied in the form of a powder without any carrier substance. A typical range of the composition will include 0.1 to 95% by weight of the composition of the N,N-dihaloamino acid, for example, 0.1 to 50%, or 0.1 to 10%, for example, 0.5 to 5%. In solutions, usually a lower concentration of the N,N-dihaloamino acid will be applied. For example, a concentration of 1 to 2% may be appropriate in case of a rinse or spray.

In case of nasopharyngeal application a catheter for nasal application containing a 1% solution of the N,N-dihaloamino acid or its salt with a pH of 3.5 to 5 may be used for several weeks using about 10 to 15 ml of the solution for each treatment. After each treatment the rinsing solution will be suctioned off.

Specific Methods for Using the Compositions of the Invention

In one aspect, the compositions of the invention are administered or used topically.

The acidic solutions of the present invention may be used in treating a number of patients with deep wounds, which do not respond to usual medications and locally applied treatments. In one aspect, the present invention provides a method for the treatment of various medical conditions such as promoting wound healing, reduction of pathogens in open wounds, wound decontamination, ocular disinfection or decontamination, oral disinfection, antifungal therapy, ophthalmic applications, reduction of pathogens in pulmonary infections, reduction of pathogens in burns, lavage, reduction of infectious load in organs for transplantation, reduction of bacterial load in autologous or artificial tissue transplantation, oral disinfection antifungal therapy, treatment of biofilm for cystic fibrosis and related diseases, treatment of viral infections, treatment of skin diseases, and tissue repair and regeneration, which method comprises using the solution of the present invention by applying the solution to the site where treatment is required. Non-limiting examples of biofilm that may be treated using the solutions of the present invention include those cited in the review article entitled "*Is there a role for quorum signals in bacterial biofilms?*" by S. Kjelleberg, and S. Molin, PMID: 12057677 (PubMed-indexed for MEDLINE).

The solutions of the invention may be effective in reducing bacterial load thus improving wound healing. The solutions could be well tolerated, improve the granulation of wound tissue, reduce the need for debridement compared to prior art solutions with patients reporting less pain during their treatment.

Oral Care

The acidic solution of the invention may be used to treat canker sores (mouth ulcers) or cold sores by rinsing the affected area. For example, the solution can be used by soaking the cold sore 3-4 times a day, each time with 2-3 applications, and putting the solution in contact with the sore for 20-30 seconds. The solution may also be used as a mouth rinse for dental and mouth hygiene and to control infection. In this instance, the solution may be used as a gargling solution to fight throat infection. The solution may be applied with the help of a cotton swab for more specific areas. The solution can be used once or several times a day according to a patient's needs and condition.

Ophthalmic Care

The physiologically-balanced, acidic solution of the invention may be used in place of a saline solution to remove a foreign body from, to rinse, or to irrigate the eyes. It can also be applied topically before or after surgery to disinfect an eye and surrounding tissues. The solution can be used once or several times a day according to a patient's needs and condition. The solution can be applied by dropping it directly into the eyes as necessary. It can also be applied by soaking a gauze and applying the saturated gauze to the eyes for 1 or several minutes. It can also be used to clean the eyes by gently wiping the eyes with saturated gauze. The solution can also be poured into a small eye washer, then the washer is inverted over the eye and the eyelid opened and closed several times.

The physiologically-balanced, acidic solution of the invention may be used for the treatment of ocular disinfection or decontamination. In addition, it may be used as a replacement for silver nitrate in the disinfection of the eyes of neonates.

The solutions of the present invention may be used for the cleaning eyes in adults and in pediatrics. For example, various viral infections, bacterial or fungal infections, or pathogenic agents may be effectively treated with the solution of the present invention. Non-limiting examples of pathogenic agents that could be successfully treated with the solution of the present invention include chlamydia trachomatis, gonorrhea as well as other bacterial, fungal, and viral infections.

The reader will see that the solution of the invention has applications in the treatment of many different types of wounds, including, without limitation, diabetic ulcers, gangrene, venous ulcers, decubitus ulcers, pressure ulcers, wounds due to bites, acute trauma wounds, surgical wounds and burns. The composition of the invention is also useful as an irrigation solution, for example, during dental, periodontal, and ophthalmic procedures. The composition of the invention can also be used for pre- and post-operative cleaning of tissue sites, and as a gargling solution for treatment of canker sores.

Methods of Using a Solution for Skin Disinfection:

The solution of the present invention may also be used to treat skin that is infected. In a skin of a patient showing medical signs of infection, the solution of the present invention may be applied directly to the area of the skin that is infected. After at least one application of the solution onto the infected skin using standard methods of application known in the art, the disinfective properties of the solution may be noted.

Reduction of Pathogens in Pulmonary Infections:

The solution of the present invention may be used for the reduction of pathogens in pulmonary infections. For example, various viral or bacterial and fungal infections may be effectively treated with the solution of the present invention. Non-limited examples of infections that may be effectively treated using the solution of the present invention include anthrax spores present in the lungs, and the reduction of pneumonia causing bacteria in the lungs, including strep bacteria and the like.

Methods of Using the Solutions of Invention in Gynecology:

The composition of the present invention may be used for the treatment of gynecological infections, such as urinary tract infections and the like. For example, various microorganisms, yeasts (e.g., *Monilia, Candida albicans,* etc), bacterial infections, HSV-2, HIV or other pathogenic agents may be effectively treated with the solution of the present invention. Optionally, the application of the solutions of the present invention can be used with other medications for the treatment of gynecological infections. For example, use as a lavage of birth canal in pregnant female patients with suspected venereal diseases, and potentially as bathing and cleansing solution on babies right after birth in the deliver rooms of hospitals or as disinfectant on catheters and shunt in dialysis room.

Method of Use as a Treatment for Topical Infections

The compounds of the current invention may be used to treat topical infections by incorporating them into creams, ointments or lotions for use in such conditions. Such creams, ointments or lotions might be used a broad variety of skin conditions and may incorporate penetration enhancers in order to deliver the antimicrobial activity of the compound to microbes present beneath the outer (epidermis) layers of the skin.

Method of Use to Prevent Surgical Site Infections

Isotonic solutions of the present invention may be used as an irrigant during surgery in order to prevent the development of surgical site infections, that frequently lead to prolonged hospitalizations and, occasionally, in death. The use of a solution of the present invention in place of saline could substantially reduce the risks of such infections especially in the case of gastric surgery and of prolonged operations, where the rate of infections may be as high as 10%.

Method of Use for Disinfection of Medical Devices and Surgical Implements

The solution of the present invention may be used for the reduction of pathogens on the surfaces of medical devices and surgical implements to prevent infection to the patient on whom the implements and devices are used, or in whom they are implanted.

The solution may also be used for the reduction or elimination of infections that occur at the entry ports of catheters and shunts that are particularly prone to such infections.

Method of Use for Surface Disinfection

The solution of the present invention may be applied directly or through delivery from a device that creates a mist (aerosolization) to the surfaces of a room, vehicle interior or other such largely confined space in order to reduce or eliminate infectious pathogens that may be suspected to be present. In such an application, it could be used to decontaminate operating theaters where infectious pathogens have been detected or rooms, vehicles and other surfaces where biological warfare agents have been dispersed.

Method of Use for Improving Food Safety

The solution of the present invention may be used for reducing pathogens on food (including, without limitation, meats, fruits and vegetables). The solution could be applied as a wash or mist to the food, or the food could be dipped in the solution. Taurine would be major residual product of such application and taurine is an essential nutrient that is considered to be safe in human food.

The solution of the present invention may also be applied to surfaces and implements used in the preparation of foods to prevent the transfer of pathogens from such surfaces and implements to the food.

Method of Use as an Antimicrobial Preservative

The compounds of the present invention may be used as a means of ensuring that microbes cannot survive in solutions intended for use in injection, infusion or for use in the eye by incorporation of an appropriate amount of such compound into the solution at the time of manufacture.

Method of Use as an Antimicrobial

The solution of the present invention may be used as a means of safely and rapidly disinfecting the hands of surgeons and nurses to reduce the risk of transporting infectious agents into an operating theatre. Additionally, solution of the present invention may be used to eliminate the infectious agent from the skin of patients (pre and post operative) in the area of a surgical incision.

Method of Wound Care

Patients suffering from long-lasting non-healing wounds should be treated with the acidic composition of the present invention on a daily basis, typically about once or twice a day.

The solution of the invention may be used as follows: a gauze material or gauze pad is presoaked with enough solution to saturate it and is then squeezed to remove excess solution. This removes species present in the gauze which would react with and reduce the effectiveness of the solution of the invention. The gauze is wetted after this procedure, but not soaked. Additional solution is then applied to completely wet the gauze, which is then immediately applied to the wound. In the alternative, the gauze may be applied to the wound and then additional solution is applied. Typically the wound site is packed with the solution-soaked gauze, and optionally, a Vaseline gauze can be applied on top of the packed wound to keep it moist and free of contaminating germs. The wound site is then wrapped with wound dressings as is standard in the art. The solution may also be used to clean a wound by pouring it directly on the wound site to remove any necrotic tissue by a mechanical procedure, and also as a cleanser or irrigant.

The patient may also make use of a "wound care kit" provided by NovaCal which permits the patient to periodically pour the solution of the present invention onto the wound site without having to remove the dressing. This kit provides ease-of-use, portability and dramatically reduces exposure of the wound to/from re-infection. The wound care kit includes a package containing the solution of the invention and bandaging material. Often the kit contains a package containing the solution of the invention and a specialized bandage for use in combination with the solution. The specialized bandage keeps the skin surrounding the wound dry while the wound is treated. Further, the bandage may be applied in a physician's office or at a hospital, with the patient continuing care at home; may be applied and used at home under the instructions of a physician; or for minor injuries, the wound care kit may be used as an "over the counter" treatment by the patient alone.

Packaging for Certain Uses

In another aspect of the invention, the solutions of the present invention may be packaged to contain the solution in individual, single use containers. The single-use containers may be used for example, for application in single change of dressing or equivalents thereof. The single-use containers of the present invention may be used in conjunction with commonly used bandages. In another of the invention, a wound care kit may comprise single-use containers of the solutions of the present invention with the specialized bandages for various applications.

In another aspect of the invention, the solutions of the present invention may be produced in-situ by the use a dual-chamber apparatus or packaging as shown in the picture with or without a third mixing chamber.

Dual Chamber for Preparation of NNDCT on Site
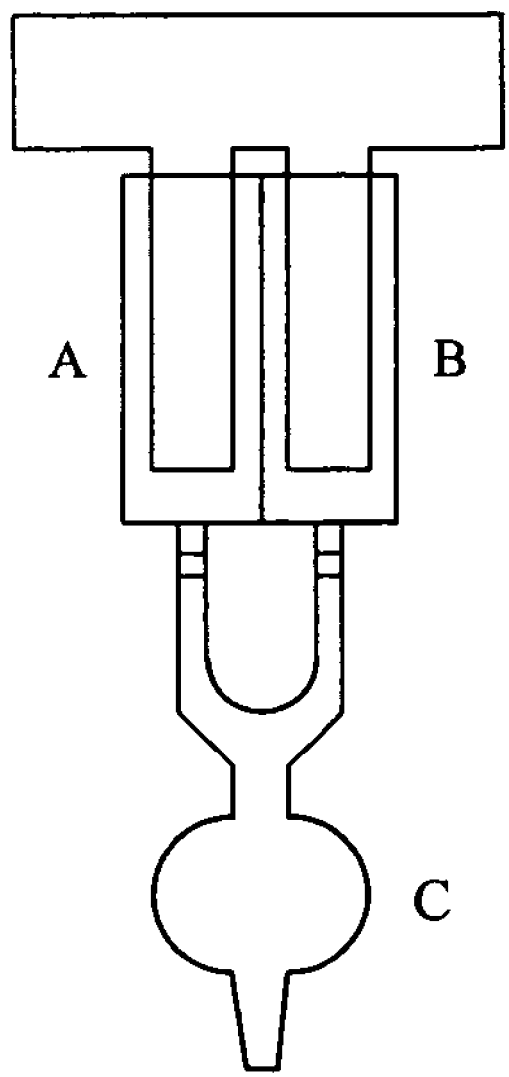

The Dual-Chamber may consist of two syringes or pouches. To make NNDCT solution with a concentration of 3.2 mM at pH 3.5, for example, chamber A is filled with 12.8 mM NaOCl solution, chamber B is filled with 3.3 mM taurine dissolved in acidified 1.8% of saline solution. The acidity of the solution in chamber B is adjusted with 1 M HCl so that when the solutions in two chambers are mixed either in a common delivery tube or in a mixing chamber C, the reaction will give desired NNDCT concentration and pH value. Since Taurine is stable in acidic solution, and NaOCl is stable at room temperature, the use of the on-site preparation method described above can avoid the stability problem of NNDCT solution.

Aspects of the Invention:

In one aspect of the invention, there is provided a pharmaceutical composition comprising an N,N-dihaloamino acid of the formula (I)

$$A\text{-}C(R^1R^\circ)R(CH_2)_n\text{—}C(YZ)\text{-}X'$$

or a derivative thereof; wherein A is hydrogen or $Hal_2N$—; Hal is halogen selected from the group consisting of chloro, bromo and iodo; R is a carbon carbon single bond or a divalent cycloalkylene radical with three to six carbon atoms; $R^1$ is hydrogen, lower alkyl or the group —COOH; $R^\circ$ is hydrogen or lower alkyl; or $R^1$ and $R^\circ$ together with the carbon atom to which they attach form a $(C_3\text{-}C_6)$cycloalkyl ring; n is 0 or an integer from 1 to 13; Y is hydrogen, lower alkyl, —$NH_2$ or —$NHal_2$; Z is hydrogen or lower alkyl; and X' is hydrogen, —COOH, —$CONH_2$, —$SO_3H$, —$SO_2NH_2$, —P(=O)(OH)$_2$ or —B(OH)$_2$; if R is a divalent cycloalkylene radical n is 0 or an integer up to and including 11, said divalent radical R or divalent radical —(CH$_2$)$_n$— being optionally substituted with —$NHal_2$; said derivative being a pharmaceutically acceptable salt, ester with lower alkanols, or lower alkanoyl derivative of the —NHgroup attached to the carbon atom to which the substituent X is attached.

In another aspect, $R^\circ$ is lower alkyl. In another aspect, R is a carbon carbon single bond and n is 0 or an integer from 1 to 7. In yet another aspect, n is 0 or an integer from 1 to 5. In one variation of the above aspects, n is 0 or an integer from 1 to 3.

In another aspect, there is provided the composition wherein the N,N-dihaloamino acid comprises 1 or 2 —$NHal_2$ groups, or wherein the N,N-dihaloamino acid comprises 1 —$NHal_2$ group. In one variation of the above, the —$NHal_2$ group is in the alpha, beta or gamma position to the group X'. In another aspect, A is —$NHal_2$. In yet another aspect, the —$NHal_2$ group is attached to the divalent radicals R or —(CH$_2$)$_n$—. In another aspect of the above, Hal is chloro.

In one aspect of the invention, said derivative is a pharmaceutically acceptable salt.

In another aspect, there is provided a composition having a concentration of the N,N-dihaloamino acid or its derivative between 0.1 to 100 mM and a pH range between about 3 to about 4.8, 3.0 to 4.5, or 3.5 to 4.5, or at about 3.5.

In another aspect of the invention, there is provided a composition with bactericidal, antibacterial, anti-infective, antimicrobial, sporicidal, disinfectant, antifungal and antiviral activity comprising an N,N-dihalo-amino acid of the formula (II)

$$Hal_2N\text{—}C(R^1R^\circ)\text{—}(CH_2)_n\text{—}C(YZ)\text{-}X \qquad (II)$$

or a derivative thereof; wherein Hal is halogen selected from the group consisting of chloro, bromo and iodo; $R^1$ is hydrogen, lower alkyl or the group —COOH; $R^\circ$ is hydrogen or lower alkyl; or $R^1$ and $R^\circ$ together with the carbon atom to which they attach form a $(C_3\text{-}C_6)$cycloalkyl ring; n is 0 or an integer from 1 to 3; Y is hydrogen, lower alkyl or —$NH_2$; Z is hydrogen or lower alkyl; and X is —COOH, —$CONH_2$, —$SO_3H$ or —$SO_2NH_2$; said derivative being selected from the group consisting of pharmaceutically acceptable salts, esters with lower alkanols, and lower alkanoyl derivatives of the —$NH_2$ group attached to the carbon atom to which the substituent X is attached; and a pharmaceutically acceptable carrier; said composition having a concentration of the N,N-dihaloamino acid or its derivative between 0.1 to 100 mM and a pH range between about 3 to about 4.8, 3.0 to 4.5, or 3.5 to 4.5, or at about 3.5.

In yet another aspect, there is provided a stabilized composition with bactericidal, antibacterial, anti-infective, antimicrobial, sporicidal, disinfectant, antifungal and antiviral activity comprising an N,N-dihalo-amino acid of the formula (II)

$$Hal_2N\text{—}C(R^1R^\circ)\text{—}(CH_2)_n\text{—}C(YZ)\text{-}X \qquad (II)$$

or a derivative thereof; wherein Hal is halogen selected from the group consisting of chloro, bromo and iodo; $R^1$ is hydrogen, lower alkyl or the group —COOH; $R^\circ$ is hydrogen or lower alkyl; or $R^1$ and $R^\circ$ together with the carbon atom to which they attach form a $(C_3\text{-}C_6)$cycloalkyl ring; n is 0 or an integer from 1 to 3; Y is hydrogen, lower alkyl or —$NH_2$; Z is hydrogen or lower alkyl; and X is —COOH, —$CONH_2$, —$SO_3H$ or —$SO_2NH_2$; said derivative being selected from the group consisting of pharmaceutically acceptable salts, esters with lower alkanols, and lower alkanoyl derivatives of the —NHgroup attached to the carbon atom to which the substituent X is attached; and a pharmaceutically acceptable carrier; said composition having a concentration of the N,N-dihaloamino acid or its derivative between 0.1 to 50 mM and a pH range between about 2 to about 7, 3 to 6, 3 to 4.8, 3 to 4.5, or 3.5 to 4.5, or at about 3.5.

In one aspect of the above, the composition is in a receptacle ensuring its long-term stability required by its bactericidal, antibacterial, anti-infective, antimicrobial, sporicidal, disinfectant, antifungal or antiviral use.

In yet another aspect, there is provided a composition comprising an N,N-dihalo-amino acid of the formula (II)

$$Hal_2N\text{—}C(R^1R^\circ)\text{—}(CH_2)_n\text{—}C(YZ)\text{-}X \qquad (II)$$

or a derivative thereof; wherein Hal is halogen selected from the group consisting of chloro, bromo and iodo; $R^1$ is hydrogen, lower alkyl or the group —COOH; $R^\circ$ is hydrogen or lower alkyl; or $R^1$ and $R^\circ$ together with the carbon atom to which they attach form a $(C_3\text{-}C_6)$cycloalkyl ring; n is 0 or an integer from 1 to 3; Y is hydrogen, lower alkyl or —$NH_2$; Z is hydrogen or lower alkyl; and X is —COOH, —$CONH_2$, —$SO_3H$ or —$SO_2NH_2$; said derivative being selected from the group consisting of pharmaceutically acceptable salts, esters with lower alkanols, and lower alkanoyl derivatives of the —$NH_2$ group attached to the carbon atom to which the substituent X is attached; and a pharmaceutically acceptable carrier; said composition having a pH range between about 2 to about 7, 3 to 6, 3 to 5, or at about 3.5, and said compositions having bactericidal, antibacterial, anti-infective, antimicrobial, sporicidal, disinfectant, antifungal and antiviral activity. In one variation, the concentration of the N,N-dihaloamino acid or its derivative between 0.1 to 100 mM, preferably 0.3 to 50 mM. In another aspect, the composition is in stabilized form. In yet another aspect, the composition is stored in a receptacle ensuring its long-term stability required by its bactericidal, antibacterial, anti-infective, antimicrobial, sporicidal, disinfectant, antifungal or antiviral use.

In one aspect of the invention, there is provided a composition comprising an N,N-dihalo-amino acid of the formula (II)

$$Hal_2N-C(R^1R^o)-(CH_2)_n-C(YZ)-X \qquad (II)$$

or a derivative thereof; wherein Hal is halogen selected from the group consisting of chloro, bromo and iodo; $R^1$ is hydrogen, lower alkyl or the group —COOH; $R^o$ is hydrogen or lower alkyl; or $R^1$ and $R^o$ together with the carbon atom to which they attach form a $(C_3-C_6)$cycloalkyl ring; n is 0 or an integer from 1 to 3; Y is hydrogen, lower alkyl or —NH$_2$; Z is hydrogen or lower alkyl; and X is —COOH, —CONH$_2$, —SO$_3$H or —SO$_2$NH$_2$; said derivative being selected from the group consisting of pharmaceutically acceptable salts, esters with lower alkanols, and lower alkanoyl derivatives of the —NH$_2$ group attached to the carbon atom to which the substituent X is attached; and a pharmaceutically acceptable carrier; said composition having a pH range between about 2 to about 7, 3 to 6, 3 to 5, or at about 3.5 in the preparation of a medicament for bactericidal, antibacterial, anti-infective, antimicrobial, sporicidal, disinfectant, antifungal and antiviral use.

In another variation, the composition has a concentration of the N,N-dihaloamino acid or its derivative between 0.1 to 100 mM, or 0.3 to 50 mM. In another variation, said medicament is in a receptacle ensuring its long-term stability required by its bactericidal, antibacterial, anti-infective, antimicrobial, sporicidal, disinfectant, antifungal or antiviral use.

In one variation, there is provided a method of preventing or treating an infection caused by a bacterial, a microbial, a sporal, a fungal or a viral activity in a mammal, said method comprising the administration of a bactericidal, antibacterial, anti-infective, antimicrobial, sporicidal, disinfectant, antifungal and antiviral amount of an N,N-dihalo-amino acid of the formula (II)

$$Hal_2N-C(R^1R^o)-(CH_2)_n-C(YZ)-X \qquad (II)$$

or a derivative thereof; wherein Hal is halogen selected from the group consisting of chloro, bromo and iodo; $R^1$ is hydrogen, lower alkyl or the group —COOH; $R^o$ is hydrogen or lower alkyl; or $R^1$ and $R^o$ together with the carbon atom to which they attach form a $(C_3-C_6)$cycloalkyl ring; n is 0 or an integer from 1 to 3; Y is hydrogen, lower alkyl or —NH$_2$; Z is hydrogen or lower alkyl; and X is —COOH, —CONH$_2$, —SO$_3$H or —SO$_2$NH$_2$; said derivative being selected from the group consisting of pharmaceutically acceptable salts, esters with lower alkanols, and lower alkanoyl derivatives of the —NH$_2$ group attached to the carbon atom to which the substituent X is attached; and a pharmaceutically acceptable carrier. In another variation, said composition has a pH range between about 2 to about 7, 3 to 6, 3 to 5, or at about 3.5. In another aspect, said composition has a concentration of the N,N-dihaloamino acid or its derivative between 0.1 to 100 mM, or 0.3 to 50 mM. In yet another aspect of the invention, said composition is in stabilized form.

In another aspect of the invention, said composition being in a receptacle ensuring its long-term stability required by its bactericidal, antibacterial, anti-infective, antimicrobial, sporicidal, disinfectant, antifungal or antiviral use.

In one aspect, the composition is isotonic and physiologically balanced.

In another aspect, the composition has a therapeutic index of about 1000 to about 5,000, defined by the ratio of its IC$_{50}$ at one hour against both L929 mouse lung epithelial cells and primary human fibroblasts to its Minimum Bactericidal Concentration against *Escherichia coli* at one hour.

In one aspect, there is provided a composition with bactericidal, antibacterial, anti-infective, antimicrobial, disinfectant, antifungal, sporicidal and antiviral activity comprising an N,N-dihalo-amino acid of the formula (IV)

$$Hal_2N-C(R^1R^2)-(CH_2)_n-C(YZ)-X \qquad (IV)$$

or a derivative thereof; wherein Hal is halogen selected from the group consisting of chloro, bromo and iodo; $R^1$ is hydrogen, lower alkyl or the group —COOH; $R^2$ is lower alkyl; or $R^1$ and $R^2$ together with the carbon atom to which they attach form a $(C_3-C_6)$cycloalkyl ring; n is 0 or an integer from 1 to 3; Y is hydrogen, lower alkyl or —NH$_2$; Z is hydrogen or lower alkyl; and X is —COOH, —CONH$_2$, —SO$_3$H or —SO$_2$NH$_2$; said derivative being selected from the group consisting of pharmaceutically acceptable salts, esters with lower alkanols, and lower alkanoyl derivatives of the —NH$_2$ group attached to the carbon atom to which the substituent X is attached. In one variation, $R^1$ is hydrogen, or lower alkyl; n is 0, 1 or 2; Y is hydrogen or lower alkyl; Z is hydrogen or lower alkyl; and X is —SO$_3$H or —SO$_2$NH$_2$; or a derivative thereof; said derivative being selected from the group consisting of pharmaceutically acceptable salts or esters with lower alkanols. In another variation, Y and Z are both hydrogen; X is —SO$_3$H; said derivative being selected from the group consisting of pharmaceutically acceptable salts. In another aspect of the above, the composition comprises a pharmaceutically acceptable carrier.

In one aspect of the above composition, the pH range is between about 2 to about 7, 3 to 6, 3 to 5, or about 3.5. In another aspect of the above, said composition is isotonic and physiologically balanced.

In one aspect of the invention, the N,N-dihaloamino acid is a member selected from the group consisting of N,N-dichloro-2,2-dimethyltaurine, N,N-dichloro-1,1,2,2-tetramethyltaurine, N,N-dibromo-2,2-dimethyltaurine, N,N-dibromo-1,1,2,2-tetramethyltaurine, N,N-diiodotaurine, N,N-dichloro-2-methyltaurine, N,N-dichloro-2,2,3,3-tetramethyl-β-alanine, N,N-dichloro-3,3-dimethylhomotaurine, N,N-dichloro ethanesulfonic acid, N,N-dichloro-1-methyl ethanesulfonic acid or a derivative thereof; said derivative is selected from the group consisting of pharmaceutically acceptable salts and esters with lower alkanols.

In yet another aspect of the invention, there is provided a method for controlling or preventing the growth of bacteria, microbes, spores, fungi or viruses or the proliferation of infections and the source of infections, said method comprising the application of an effective amount of a composition of the present invention to an area, space or material requiring said control or prevention of growth or proliferation. In one variation, the pH of the composition is between about 2 to about 7, 3.0 to 6.8, 3 to 6, 3 to 5, or about 3.5.

In one aspect of the above methods, said N,N-dihalo amino acid or derivative thereof is prepared in situ. In one variation of the above methods, the material to be treated is selected from the class consisting of food, animal feed, surgical instruments, surgical equipment, medical devices and equipment used for such purposes.

In one aspect, the invention provides an N,N-dihaloamino acid of the formula (IV)

$$Hal_2N-C(R^1R^2)-(CH_2)_n-C(YZ)-X$$

or a derivative thereof; wherein Hal is halogen selected from the group consisting of chloro, bromo and iodo; $R^1$ is hydrogen, lower alkyl or the group —COOH; $R^2$ is lower alkyl; or $R^1$ and $R^2$ together with the carbon atom to which they attach form a $(C_3-C_6)$cycloalkyl ring; n is 0 or an integer from 1 to 3; Y is hydrogen, lower alkyl or —$NH_2$; Z is hydrogen or lower alkyl; and X is —COOH, —$CONH_2$, —$SO_3H$ or —$SO_2NH_2$; said derivative being selected from the group consisting of pharmaceutically acceptable salts, esters with lower alkanols, and lower alkanoyl derivatives of the —$NH_2$ group attached to the carbon atom to which the substituent X is attached. In one variation of the N,N-dihaloamino acid, $R^1$ is hydrogen, or lower alkyl; n is 0, 1 or 2; Y is hydrogen or lower alkyl; Z is hydrogen or lower alkyl; and X is —$SO_3H$ or —$SO_2NH_2$; or a derivative thereof; said derivative being selected from the group consisting of pharmaceutically acceptable salts or esters with lower alkanols. In another variation, Y and Z are hydrogen; X is —$SO_3H$; said derivative being selected from the group consisting of pharmaceutically acceptable salts.

In one aspect of the invention, the composition is selected from the group consisting of N,N-dichloro-2,2-dimethyltaurine; N,N-dichloro-1,1,2,2-tetramethyltaurine; N,N-dibromo-2,2-dimethyltaurine; N,N-dibromo-1,1,2,2-tetramethyltaurine; N,N-dichloro-2-methyltaurine; N,N-dichloro-2,2,3,3-tetramethyl-β-alanine; N,N-dichloro-3,3-dimethylhomotaurine; and N,N-dichloro-1-methylethanesulfonic acid or a pharmaceutically acceptable salt thereof.

In one variation of the N,N-dihaloamino acid, Hal is chloro, or a pharmaceutically acceptable salt thereof.

In another aspect, there is provided a pharmaceutical composition comprising an N,N-dihalo amino acid of the invention, or a derivative thereof.

In yet another aspect, there is provided a method of preventing or treating an infection caused by a bacterial, a microbial, a sporal, a fungal or a viral activity in a mammal, said method comprising the administration of a bactericidal, antibacterial, anti-infective, antimicrobial, sporicidal, disinfectant, antifungal and antiviral amount of an N,N-dihalo-amino acid of the invention.

In another variation, the invention provides a method for controlling or preventing the growth of bacteria, microbes, spores, fungi or viruses or the proliferation of infections and the source of infections, said method comprising the application of an effective amount of said N,N-dihalo amino acid above to an area, space or material requiring said control or prevention of growth or proliferation.

In one variation, the composition has a concentration of the N,N-dihaloamino acid or its derivative between 0.1 and 100 mM or 0.3 to 50 mM and a pH range between about 3 to about 4.8, 3.0 to 4.5, or 3.5 to 4.5, or at about 3.5.

In another aspect, the composition is in stabilized form, said composition having a concentration of the N,N-dihaloamino acid or its derivative between 0.1 and 100 mM or 0.1 to 50 mM and a pH range between about 2 to about 7, 3 to 6, 3 to 4.8, 3 to 4.5, or 3.5 to 4.5, or at about 3.5. In one variation said composition being in a receptacle ensuring its long-term stability required by its bactericidal, antibacterial, anti-infective, antimicrobial, sporicidal, disinfectant, antifungal or antiviral use.

In one aspect of the invention, there is provided the use of an N,N-dihalo-amino acid of the invention in the preparation of a bactericidal, antibacterial, anti-infective, antimicrobial, sporicidal, disinfectant, antifungal and antiviral activity composition.

EXAMPLE 1

Method of Preparation

Reagents: All solutions were made with deionized, or Millipore water. NaOCl (6%) solution was purchased from VWR. Taurine was purchased from Sigma. NaCl and HCl are reagent-grade.

Synthesis and Characterization of N,N-Dichlorotaurine (NNDCT)

In this study, NNDCT was prepared by dissolving taurine powder in HOCl solution (pH 3.5) at a HOCl/Taurine ratio of 2.

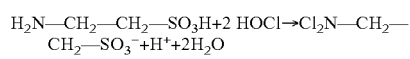

To make 1 liter of 1.6 mM of NNDCT in 0.9% NaCl solution at pH 3.5, add 8.6 g of NaCl into a 1000-ml volumetric flask, then add 500 ml Millipore water into the flask to dissolve the salt. Add 2 ml of 1 M HCl into the NaCl solution, followed by adding 22 ml of 0.158 M NaOCl. Mix the solution. Then add 0.267 g of taurine into the flask and fill the volumetric flask up to the mark with Millipore water. Stir the solution for 5 minutes.

NNDCT has a maximum absorbance at 300 nm with a molar absorptivity of 370 $M^{-1}$ $cm^{-1}$. When $OCl^-$ solution (pH 9.5) was added into the taurine solution, N-Chlorotaurine (NCT) (ClHN—$CH_2$—$CH_2$—$SO_3^-$) was the only product formed.

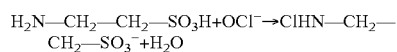

NNDCT and NCT are spectrophotometrically distinguishable. NCT has a maximum absorbance at 252 nm. The yield of NNDCT was calculated from its absorbance at 300 nm. This preparation method gives a yield of 91% of NNDCT. Iodometric titration gives a $I_2$/NNDCT ratio of 2. This suggests that NNDCT retains the two oxidizing equivalents of HOCl. Both chlorine moieties in NNDCT are able to oxidize the $I^-$ to $I_2$. NNDCT decomposes in solution, but it is more stable at low temperature. A stability study on NNDCT solution (pH 3.5) was performed at three temperatures, 4° C., room temperature and 40° C. The solution was sealed in ampoules. The stability of NNDCT at three temperatures is in the following order: 4° C.>room temperature>40° C. In 4 weeks, 5.4% of NNDCT is lost when stored in refrigerator (4° C.) ($[NNDCT]_{initial}$=1.47 mM).

N,N-dichlorotaurine is very soluble in water at a pH range from 1 to 10. N,N-dichlorotaurine can be identified and quantitatively determined by UV spectroscopy. N,N-dichlorotaurine has a maximum UV absorbance at 300 nm and a molar absorptivity of 370 $M^{-1}$ $cm^{-1}$.

NNDCT is not volatile. A solution of 1.47 mM in 0.9% saline at pH 3.5 was filled in two glass bottles. One bottle was capped tightly and another was capped loosely. There was no difference in the concentration of NNDCT in two bottles after 4 weeks at room temperature.

Isolation of the pure powder form of NNDCT and storage under inert atmosphere provides a more stable source for NNDCT. Additionally, reformulation of the solid matrix of NNDCT in a pill format assists in the stabilization of NNDCT. This pill formulation has been selected to prevent decomposition while providing ease of use in the intended pharmaceutical application (contact lens disinfections, other application).

EXAMPLE 2

Antimicrobial Activity

Bactericidal Activity:

To determine the bactericidal activity, we used *Escherichia coli* (ATCC 11229). The bacterial culture was diluted in sterile saline to prepare inocula. Various test articles were transferred to individual tubes already containing $1.0 \times 10^5$ to $2.0 \times 10^5$ Colony Forming Units (CFU)/mL bacteria and mixed by gentle vortexing and then incubated at 37° C. for 1 or 24 hours. In an attempt to mimic as far as possible the conditions, which could be produced in vivo if the test articles were used as antiseptics, bacterial plating in a Petri dish was performed immediately after the designated exposure time without the addition of a neutralizer, and independently with addition of neutralizer (as control). Thus, 0.1 mL was removed after 1 or 24 hours exposure times and plated. Plates were incubated at 37° C., and the numbers of bacteria were counted by direct colony count to numerate the surviving bacteria as CFU/mL. Positive growth controls were made with sterile 0.9% saline. All test articles were tested three times. The results were tabulated to show the comparison of antimicrobial effectiveness range of HOCl, OCl$^-$, NNDCT and 0.9% saline at various pH levels. At pH 3.5 NNDCT showed an effective antimicrobial concentration range between 0.0149 to 1.49 mM at 60 min, and an effective antimicrobial concentration range between 0.000149 to 1.49 mM at 24 hrs, whereas the effective antimicrobial concentration range for HOCl commenced at 0.016 at 60 min and at 0.0016 mM at 24 hrs. At pH 3.5 NNDCT was better or as effective against *E. coli* as HOCl.

In these studies for the first time we have demonstrated (in parallel) the bactericidal and cell toxicity profiles of N-Chloramines as compared to various test articles. Both N-Chlorotaurine (NCT) and N, N-Dichlorotaurine (NNDCT) were synthesized in 0.9% physiological concentration of NaCl with controlled pH according to procedures described above. These solutions were tested for their physicochemical properties before analyzing their biological activities. Diluted solutions of NCT and NNDCT are colorless and isotonic and display exceptionally rapid antimicrobial activity. Production of these oxidants appears to be pH-dependent. NCT is formed exclusively in alkaline pH, whereas NNDCT is formed in acidic pH.

Comparative antimicrobial assays using NNDCT in the solution of the present invention at pH 5.0 and 3.5 and NCT at pH 9.5 demonstrated a bacterial (*E. coli*) killing efficiency of about 300 fold greater for NNDCT at pH 3.5 over NNDCT at pH 5.0 and 1000 fold higher killing efficiency of NNDCT at pH 3.5 as compared to NCT at pH 9.5 within the 60 min exposure time at 37° C. (Table-1).

TABLE 1

| | Product summary: | | | | |
|---|---|---|---|---|---|
| Product | Color | pH | Tonicity | Physical Status | MBC (μg/mL) |
| NCT | clear | 9.5 | Isotonic | solution | 142.5 |
| NNDCT | clear | 5.0 | Isotonic | solution | 38.0 |
| NNDCT | clear | 3.5 | Isotonic | solution | 0.136 |

MBC is the Minimum Bactericidal Concentration

The antimicrobial activity and killing time not only were concentration dependent but also increased markedly by lowering the pH. NCT is less antimicrobial than NNDCT on an equal concentration basis by a factor of 1000 fold.

EXAMPLE 3

Cytotoxicity Assay:

Cytotoxicity was assessed by a colorimetric assay system, initially described by Scudiero et al., using 3'-(phenylaminocarbonyl)-3,4-tetrazolium-bis (4-methoxy-6-nitro) benzene sulfonic acid hydrate (XTT), ProCheck™ cell viability assay (Evaluation of a soluble tetrazolium/formazan assay for cell growth and drug sensitivity in culture using human and other tumor cell lines described by Scudiero D A, Shoemaker R A H, Paul K D, Monks A, Tierney S, Nofziger T H, Currens M J, Seniff D, Boyd M R. Cancer Res. 1988 Sep. 1; 48(17): 4827-33). Similar approaches for determining the cell viability are used by other investigators. Three cell types were used: mouse lung epithelial cells (L929), primary human skin fibroblast and primary human keratinocyte cells cultured in Dulbecco Modified Eagle's Medium and Keratinocyte defined medium with corresponding growth factors plus antibiotics. Cells were trypsinized and counted under the microscope and seeded at 1000-to-2000 cells per well of a flat-bottom 96-well plate. Cells were allowed to grow over-night at 37° C. Next day, tissue culture media was removed and cells were rinsed with fresh media 1× and then left in 50 μL of tissue culture media. Test articles were prepared as 2-fold dilutions and 200 μL was added into each set of 4-wells (total volume per well=250 μL). Cells were exposed to test articles for 60 min at room temperature. Immediately after the exposed time, test article from each well was removed and cells were fed with 250 μL of fresh media. Plates were incubated at 37° C. for 18-20 hours. The following day media was removed again and replaced with 100 μL/well of fresh media containing 10/100 μL XTT-reagent. Cells were incubated under growth conditions (5% $CO_2$ at 37° C. humidified incubator), protected from light, until color development was achieved. Absorbance was read at 450 nm with reference wavelength at 750 nm using Molecular Device ThermoMax Plate reader, blanking the plate on the medium-only assay blank wells. Untreated cells receiving XTT reagents-only served as positive cell proliferation control.

When cell inhibitory concentration toxicity index ($CCI_{50}$) was determined (measured as 50% of cells still alive), $CCI_{50}$ of NNDCT was at 7 mM and showed a substantially higher cell viability of Primary Human Skin Fibroblasts in the XTT Assay than for $CI_{50}$ of HOCl ($IC_{50}$=0.8 mM), betadine ($IC_{50}$=0.01 mM) or OCl$^-$ ($IC_{50}$=0.66 mM). Similar results were attained in the XTT Assay performed on mouse lung epithelial cells (L929) where more than 90% viability for NNDCT was observed at a concentration of 7 mM versus substantially less than 50% viability for OCl$^-$ at concentrations of 0.6 mM and betadine at concentrations of 0.02 mM.

Cytotoxicity and Therapeutic Index

NNDCT has been subjected to rigorous in vitro safety testing using United States Pharmacopoeia's standard cell assay (mouse lung epithelial cells, L929), as well as primary human skin cells. We discovered that NNDCT has a very low cell toxicity index in both cell types: Primary human fibroblast and L929 cells as compared to other antiseptic test articles: HOCl and Povidone-Iodine (see below). Unlike Povidone Iodine where cell toxicity was a major concern, NNDCT demonstrated to be cell compatible with a much safer toxicity profile. In fact, the therapeutic index (TI), which is defined as the ratio of a concentration tolerated by the assayed cells (in vitro cytotoxicity or $ICI_{50}$) over the Minimum Bactericidal Concentration (MBC) for NNDCT was about 5,000 as compared to about 300 and 7 for HOCl and Povidone-Iodine, respectively (Table 2).

TABLE 2

Summary of Minimum Bactericidal Concentration (MBC) and Therapeutic Index data

| Product | pH | MBC[a] (µg/mL) | IC$_{50}$ (µg/mL) | T.I[b]. on HF[c] |
|---|---|---|---|---|
| NNDCT | 3.5 | 0.29 | 1442 | 4972 |
| HOCl | 3.5 | 0.16 | 47 | 297 |
| Povidone-Iodine | 4.2 | 0.38 | 2.5 | 7 |

[a]Minimum Bactericidal Concentration (MBC)
[b]Therapeutic Index and
[c]Primary human skin fibroblast cells.

Application of NNDCT as safer topical disinfectant particularly in ophthalmic, chronic non-healing wounds and burn patients could be a great advantage, because use of other disinfectants with major toxic side effects is highly discouraged by healthcare authorities. Since food safety is also a major health issue, the application of NNDCT as a broad disinfectant can be extended to food industry.

EXAMPLE 4

As an example, the procedure for the preparation of N,N-dichloro-1,1-dimethylethanesulphonic is described as follows:

Step 1. Synthesis of 1,1-dimethylethanesulphonic acid (Braghiroli, D.; Bella, M. D. Tetrahedron Letters, 1996, 37, 7319-7322).

1,1-dimethylethanesulphonic acid is prepared by reduction of 2-hydroxyisobutyronitrile (acetone cyanohydrin) to 1-amino-2-methyl-2-propanol, followed by protection with (Boc)$_2$O. After mesylation and removal of the protecting group, the hydrochloride obtained was allowed to react with sodium sulfite to give 1,1-dimethylethanesulphonic acid.

Step 2 Chlorination of 1,1-dimethylethanesulphonic acid.

To make 1 liter of 1.6 mM of N,N-Dichloro-1,1-dimethylethanesulphonic acid (NNDC-DMESA) in 0.9% NaCl solution at pH 3.5, add 8.6 g of NaCl into a 1000-ml volumetric flask, then add 500 ml Millipore water into the flask to dissolve the salt. Add 2 ml of 1 M HCl into the NaCl solution, followed by adding 22 ml of 0.158 M NaOCl. Mix the solution. Then add 0.355 g of 1,1-dimethylethanesulphonic acid into the flask and fill the volumetric flask up to the mark with Millipore water. Stir the solution until the reaction is completed as indicated for example by UV or NMR.

We have prepared N,N-chlorinated ornithine, N,N-dichloro homotaurine and N,N-dichloro alanine. All these dichloro compounds have very similar UV spectra ($\lambda_{max}$=~300 nm) and molar absorptivities.

Procedure for Preparing the Dichloro-Amino Acid Compounds

Into an acidic HOCl solution, a stoichiometric amount of amino acid or their salt (powder) is added (the molar ratio of HOCl: amino acid=2:1). Then the mixture solution is stirred for about 15 minutes. The pH of the resulting solution is lower than the pH of the starting HOCl solution. The product is identified and the completion of the reaction is followed by an UV-vis spectrophotometer. The pH of the solution is adjusted with hydrochloric acid or sodium hydroxide solution to the desired pH value. The concentration of the solution is determined on UV spectrophotometer by using the corresponding molar absorptivity at the $\lambda_{max}$. A more detailed procedure is described in the following example.

EXAMPLE

Preparing 1 Liter of 0.05 M of Dichloro Homotaurine Solution

Step 1. Prepare 1 liter of 0.1 M HOCl solution with a pH<5.
Step 2. Add 8.06 g of sodium homotaurine (sodium 3-amino-1-propansulfonic, MW=161.13) into the HOCl solution in step 1. Stir the solution for about 15 minutes.
Step 3. Take an aliquot of solution in step 2 and make 100-fold dilution. Take the UV spectrum of the diluted solution to identify the product, which has $\lambda_{max}$ at 303 nm (see the attached table).
Step 4. Adjust the pH of the solution resulted in step 2 to the desired pH with NaOH or HCl.
Step 5. Repeat the procedure in step 3 to measure the concentration of the dichloro homotaurine (the molar absorptivity is 329.0 $M^{-1}$ $cm^{-1-}$, see the attached table).

TABLE

Molar Absorptivities of N,N-Dichloro- and N,N-dibromo-Amino Acid Compounds

| Compounds | $\lambda_{max}$ (nm) | $\epsilon$ ($M^{-1}cm^{-1}$) |
|---|---|---|
| N,N-dichloro taurine | 302 | 332.9[a] |
| N,N-dichloro homotaurine | 303 | 329.0[c] |
| N,N-dichloro β-alanine | 301 | 327.6[c] |
| N,N,N',N'-tetrachloro ornithine | 300[c,d] | 241[c,d] |
| N,N-dibromo taurine | 241 | 2713[b], 2708[c] |

[a]Gottardi, W.; Nagl, M. Arch. Pharm. Pharm. Med. Chem. 2002, 9, 411–421.
[b]Thomas, E.; Bozeman, P.; Jefferson, M.; King, C.J. Bio. Chem. 1995, 7, 2906–2913.
[c]determined in this study.
[d]based on a 4:1 molar ratio of chlorinating agent to ornithine.

EXAMPLE 5

The results of our discovery provide support for antimicrobial activity of NNDCT in 0.9% saline at pH 3.5. These antimicrobial activities were determined to be considerable in a µM range and increased significantly by increasing the concentration and or exposure time. In contrast, cell toxicity was seen at a 1000-fold higher range in the mM range. We showed that NNDCT treated cells were able to tolerated the treatment and be able to go through normal cell proliferation cycles as compared to untreated control cells in our XTT assay.

EXAMPLE 6

NNDCT solutions with a concentration of 1.49 mM at pH 3.0, 3.5, 4.0, and 5.0 were prepared. The spectra and the concentrations of the solutions were measured on the UV-vis spectrometer. The results showed that the spectrum and the concentration of NNDCT solution did not change in the pH range from 3.0 to 5.0.

Preparation

Add 8.8 g NaCl, 2 ml of 1.0 M HCl, and 0.278 g of taurine into a 1000-ml volumetric flask, followed by adding about 800 ml of deionized water into the flask. Shake the flask to dissolve NaCl and taurine powders. Then add 22 ml of 0.15M of the NaOCl solution into the flask. Fill the flask up to the mark with deionized water. Stir the solution with a magnetic stirring bar for 5 minutes. The concentration and the pH of the resulting solution were measured on a UV-vis spectrometer and a freshly calibrated Beckman pH meter. This solution has a concentration of 1.49 mM and a pH value of 3.85. 100 ml of NNDCT solution above (pH=3.85) was pipetted into a 250-ml beaker, 0.09 ml of 1.0 M HCl solution was added to this solution and stir. The final pH of this solution is 3.0. 100 ml of NNDCT solution with pH 3.85 solution was pipetted into a 250-ml beaker, 0.003 ml of 5.0 M NaOH solution was added to this solution and stir. The final pH of this solution is 4.85.

Solutions with varying pH values were prepared in a similar manner within the pH range of 3 to 5. All solutions show stability if properly stored as shown by their UV spectra.

What is claimed is:

1. An N,N-dihaloamino acid of the formula (IV)

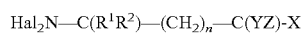

$Hal_2N—C(R^1R^2)—(CH_2)_n—C(YZ)-X$ or a derivative thereof; wherein

Hal is halogen selected from the group consisting of chloro and bromo;

$R^1$ is hydrogen, lower alkyl or the group —COOH;

$R^2$ is lower alkyl; or $R^1$ and $R^2$ together with the carbon atom to which they attach form a $(C_3-C_6)$cycloalkyl ring;

n is 0 or an integer from 1 to 3;

Y is hydrogen, lower alkyl or —$NH_2$;

Z is hydrogen or lower alkyl; and

X is —$CONH_2$, —$SO_3H$ or —$SO_2NH_2$;

said derivative being selected from the group consisting of pharmaceutically acceptable salts, esters with lower alkanols, and lower alkanoyl derivatives of the —$NH_2$ group attached to the carbon atom to which the substituent X is attached;

wherein the N,N-dihaloamino acid is selected from the group consisting of

N,N-dichloro-2,2-dimethyltaurine;
N,N-dichloro-1,1,2,2-tetramethyltaurine;
N,N-dibromo-2,2-dimethyltaurine;
N,N-dibromo-1,1,2,2-tetramethyltaurine;
N,N-dichloro-2-methyltaurine; and
N,N-dichloro-3,3-dimethylhomotaurine.

* * * * *

UNITED STATES PATENT AND TRADEMARK OFFICE
CERTIFICATE OF CORRECTION

PATENT NO.       : 7,462,361 B2                                     Page 1 of 3
APPLICATION NO.  : 10/920636
DATED            : December 9, 2008
INVENTOR(S)      : Mansour Bassiri et al.

It is certified that error appears in the above-identified patent and that said Letters Patent is hereby corrected as shown below:

IN THE SPECIFICATION

At column 1, line 32, "1-amino-1,1-dimethylethanesulfonic acid" should be replaced with --2-amino-2-methylpropanesulfonic acid--.

At column 1, line 34, "phosphopantanoic" should be replaced with --phosphopentanoic--.

At column 1, lines 34-35, "aminoethylphosponic" should be replaced with --aminoethylphosphonic--.

At column 1, line 50, "dialo" should be replaced with --dihalo--.

At column 7, line 31, "dichloro2" should be replaced with --dichloro-2--.

At column 7, line 32, "N,N-dichloro-1-methyl-ethanesulfonic acid" should be replaced with --N,N-dichloro-2-amino-1-methylethanesulfonic acid--.

At column 7, line 34, "N,N-dibromo 2-amino-5-phosphonopantanoic" should be replaced with --N,N-dibromo-2-amino-5-phosphonopentanoic--.

At column 7, line 35, "aminoethylphosponic" should be replaced with --aminoethylphosphonic--.

At column 7, line 37, "N,N-dichloro 1-amino-1-methylethane phosphonic" should be replaced with --N,N-dichloro-1-amino-1-methylethanephosphonic--.

At column 7, line 38, "N,N-dichloro 1-amino-2-methylethane phosphonic" should be replaced with --N,N-dichloro-1-amino-propanephosphonic--.

At column 7, line 40, "N,N-dichloro leucine phosphonic" should be replaced with --N,N-dichloro-leucine-phosphonic--.

Signed and Sealed this

Fifteenth Day of June, 2010

David J. Kappos
*Director of the United States Patent and Trademark Office*

CERTIFICATE OF CORRECTION (continued)
U.S. Pat. No. 7,462,361 B2

IN THE SPECIFICATION

At column 7, line 41, "N,N-dichloro 4-amino-4-phosphonobutyric" should be replaced with --N,N-dichloro-4-amino-4-phosphonobutyric--.

At column 7, line 42, "N,N-dichloro 2-amino-5-phosphonovaleric" should be replaced with --N,N-dichloro-2-amino-5-phosphonovaleric--.

At column 7, line 43, "N,N-dichloro (+)2-amino-5-phosphonovaleric" should be replaced with --N,N-dichloro-(+)2-amino-5-phosphonovaleric--.

At column 7, line 44, "N,N-dichloro d,1-2amino-3-phosphonopropionic acid" should be deleted.

At column 7, line 45, "N,N-dichloro 2-amino-8-phosphonooctanoic" should be replaced with --N,N-dichloro-2-amino-8-phosphonooctanoic--.

At column 7, line 46, "N,N-dichloro leucine boronic" should be replaced with --N,N-dichloro-leucine-boronic--.

At column 8, lines 19-20, "1-amino-1,1-dimethylethanesulfonic acid" should be replaced with --2-amino-2-methylpropanesulfonic acid--.

At column 8, line 23, "phosphonopantanoic" should be replaced with --phosphonopentanoic--.

At column 8, line 25, "aminoethylphosponic" should be replaced with --aminoethylphosphonic--.

At column 8, lines 26-27, "2-methylethane phosphonic" should be replaced with --propanephosphonic--.

At column 8, lines 30-31, "N,N-dichloro d,1-2amino-3-phosphonopropionic acid" should be deleted.

At column 24, line 39, "N,N-dichloro ethanesulfonic acid" should be replaced with --N,N-dichloro-2-aminoethanesulfonic acid--.

At column 24, line 40, "N,N-dichloro-1-methyl ethanesulfonic acid" should be replaced with --N,N-dichloro-2-amino-1-methylethanesulfonic acid--.

At column 25, lines 24-25, "N,N-dichloro-1-methyl ethanesulfonic acid" should be replaced with --N,N-dichloro-2-amino-1-methylethanesulfonic acid;--.

At column 29, lines 25-26, "N,N-dichloro-1,1-dimethylethanesulphonic acid" should be replaced with --2-(dichloroamino)-2-methylpropanesulfonic acid-- and the parenthetical phrase --(also referred to herein as N,N-dichloro-2,2-dimethyltaurine)-- should be added thereafter.

At column 29, line 28, "1,1-dimethylethanesulphonic acid" should be replaced with --2-amino-2-methylpropanesulfonic acid--.

CERTIFICATE OF CORRECTION (continued)
U.S. Pat. No. 7,462,361 B2

IN THE SPECIFICATION

At column 29, line 32, "1,1-dimethylethanesulphonic acid" should be replaced with --2-amino-2-methylpropanesulfonic acid--.

At column 29, line 37, "1,1-dimethylethanesulphonic acid" should be replaced with --2-amino-2-methylpropanesulfonic acid--.

At column 29, line 38, a --.-- should be inserted between "Step 2" and "Chlorination"; and "1,1-dimethylethanesulphonic acid" should be replaced with --2-amino-2-methylpropanesulfonic acid--.

At column 29, lines 39-40, "N,N-Dichloro-1,1-dimethyl-ethanesulphonic acid" should be replaced with --2-(dichloroamino)-2-methylpropanesulfonic acid--.

At column 29, line 45, "1,1-dimethylethanesulphonic acid" should be replaced with --2-amino-2-methylpropanesulfonic acid--.

At column 30, line 1, a --5-- should be inserted after "EXAMPLE"; at line 38, "EXAMPLE 5" should be replaced with --EXAMPLE 6--; and at line 50, "EXAMPLE 6" should be replaced with --EXAMPLE 7--.

At column 30, line 8, "1-propansulfonic" should be replaced with --1-propanesulfonic--.